United States Patent
Lewis et al.

(10) Patent No.: US 6,849,601 B1
(45) Date of Patent: Feb. 1, 2005

(54) PEPTIDES

(75) Inventors: Richard James Lewis, Woolloongabba (AU); Paul Francis Alewood, Moggill (AU); Iain Andrew Sharpe, Taringa (AU)

(73) Assignee: The University of Queensland, St. Lucia (AU)

( * ) Notice: Subject to any disclaimer, the term of this patent is extended or adjusted under 35 U.S.C. 154(b) by 0 days.

(21) Appl. No.: 09/806,376

(22) PCT Filed: Oct. 1, 1999

(86) PCT No.: PCT/AU99/00843

§ 371 (c)(1),
(2), (4) Date: Oct. 18, 2001

(87) PCT Pub. No.: WO00/20443

PCT Pub. Date: Apr. 13, 2000

(30) Foreign Application Priority Data

Oct. 2, 1998 (AU) .............................................. PP 6273

(51) Int. Cl.$^7$ .......................... C07K 7/08; C07K 14/00; C07K 14/435; A61K 38/17

(52) U.S. Cl. ............................. 514/13; 514/2; 530/324; 530/300; 435/440; 435/69.1; 424/278.1; 536/23.1

(58) Field of Search ....................... 514/2, 13; 530/324, 530/300; 435/440, 69.1, 320.1; 424/278.1; 536/23.1

(56) References Cited

FOREIGN PATENT DOCUMENTS

| WO | WO 95/11256 | 4/1995 |
|----|-------------|--------|
| WO | WO 98/24462 | 6/1998 |
| WO | WO 99/21878 | 5/1999 |
| WO | WO 99/33482 | 7/1999 |

OTHER PUBLICATIONS

Alonso, D. et al. (2003) Drugs from the sea: conotoxins as drug leads for neuropathic pain and other neurological conditions. Mini Rev Med Chem. vol. 3, pp. 785–787. Review.*

* cited by examiner

*Primary Examiner*—Jon P. Weber
*Assistant Examiner*—Samuel W. Liu
(74) *Attorney, Agent, or Firm*—Scully, Scott, Murphy & Presser

(57) ABSTRACT

The present invention relates to novel peptides and derivatives thereof useful as selective $\alpha_1$-adrenoceptor antagonists which ability of inhibiting the agonist action of agonist noradrenaline on the $\alpha_1$-adrenoceptor is greater than their ability of inhibiting the action of agonist noradrenaline on the other α-adrenoceptors. The invention also relates to pharmaceutical compositions comprising these peptides.

11 Claims, 5 Drawing Sheets

PEPTIDES

Figure 1:
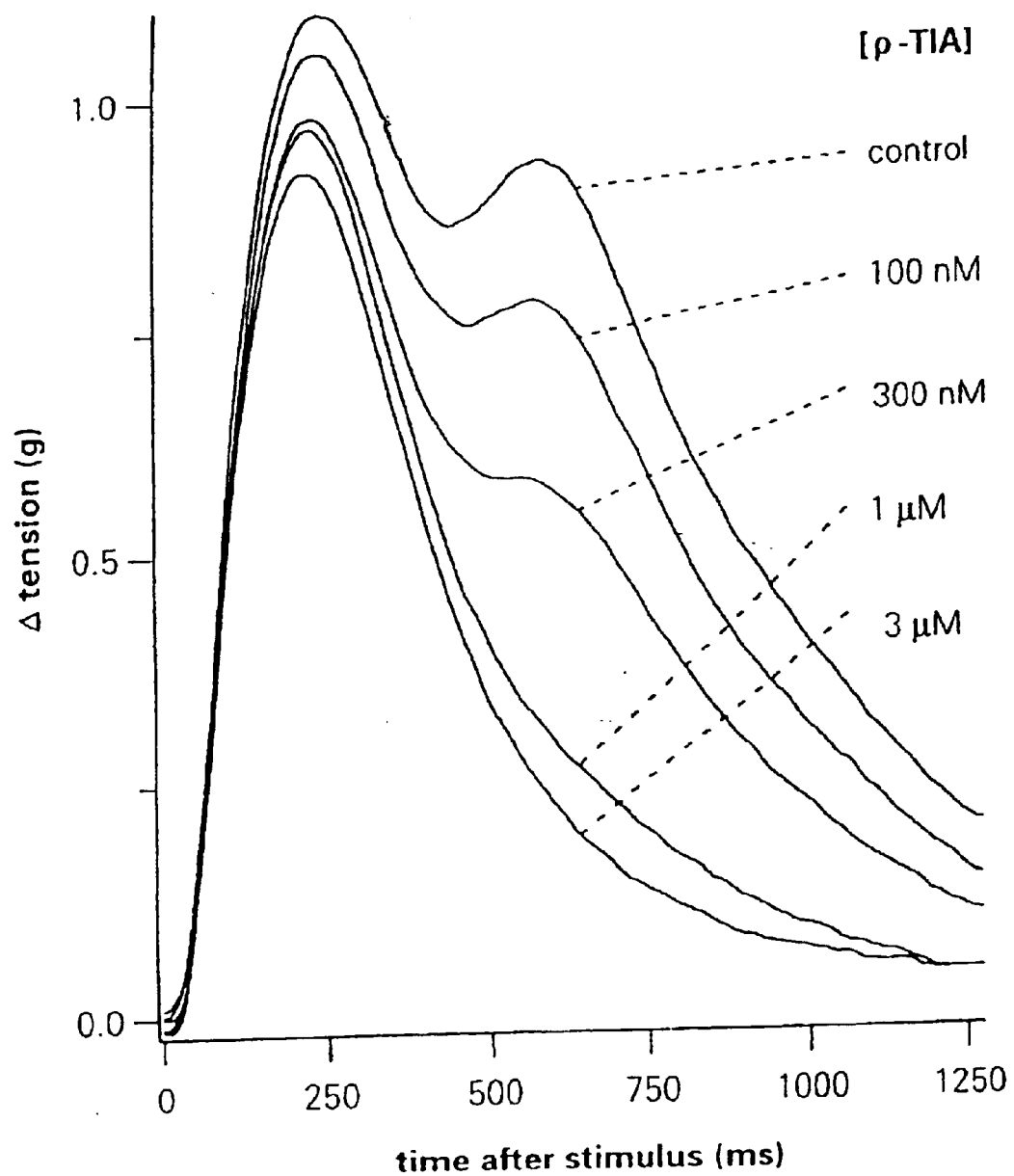

The present invention relates to novel peptides and derivatives thereof useful as selective $\alpha_1$-adrenoceptor antagonists. The invention also relates, to pharmaceutical compositions comprising these peptides, nucleic acid probes useful in finding active analogues of these peptides, assays for finding compounds having selective $\beta_1$-adrenoceptor antagonist activity and the use of these peptides in the prophylaxis or treatment of conditions such as but not limited to urinary or cardiovascular conditions.

The marine snails of the genus *Conus* (cone snails) use a sophisticated biochemical strategy to capture their prey. As predators of either fish, worms or other molluscs, the cone snails inject their prey with venom containing a cocktail of small bioactive peptides. These toxin molecules, which are referred to as conotoxins, interfere with neurotransmission by targeting a variety of receptors and ion-channels. The venom from any single *Conus* species may contain more than 100 different peptides. The conotoxins are divided into classes on the basis of their physiological targets. To date, ten classes have been described. The to-conotoxin class of peptides target and block voltage-sensitive $Ca^{2+}$-channels inhibiting neurotransmitter release. The $\alpha$-conotoxins and $\psi$-conotoxins target and block nicotinic acetylcholine (ACh) receptors, causing ganglionic and neuromuscular blockade. Peptides of the $\mu$conotoxin class act to block voltage-sensitive $Na^+$-channels, inhibiting muscle and nerve action potentials. The $\delta$-conotoxins target and delay the inactivation of voltage-sensitive $Na^+$-channels, enhancing neuronal excitability. The $\kappa$-conotoxin class of peptides target and block voltage-sensitive $K^+$-channels, and these may also cause enhanced neuronal excitability. The conopressins are vasopressin receptor antagonists and the conantokins are N-methyl-D-aspartate (NMDA) receptor antagonists. More recently, the prototype of a new $\gamma$-conotoxin class, which targets a voltage-sensitive nonspecific cation channel, and of a new $\sigma$-conotoxin class, which antagonises the $5HT_3$ receptor, have been described.

It has now been found that a new class of conotoxin exists, hereafter referred to as the $\rho$-conotoxin class, which are characterised by having $\alpha_1$-adrenoceptor antagonist activity. $\alpha_1$-Adrenoceptors play important roles in many physiological and pathophysiological processes of the cardiovascular and urogenital systems, including myocardial inotropy and chronotropy, cardiac hypertrophy and arrhythmias, vasoconstriction, smooth muscle contraction and prostate disease. $\alpha_1$-adrenoceptor antagonist drugs are of use as both tools for basic research and as therapeutic agents.

U.S. Pat. No. 5,620,993 (Patane et al) describes some of the known functions of adrenergic receptors of the $\alpha_1$-subtype, as well as some of the known pharmacological agents which bind to them. The peptides of the present invention are the first peptides reported to have $\alpha_1$-adrenoceptor antagonist activity. Further $\rho$-conotoxin peptides act non-competitively to inhibit noradrenaline action. Thus, it appears that $\rho$-conotoxins act at a site distinct from the site of noradrenaline activation and distinct from the site of action of traditional $\alpha$-adrenorecptor antagonists such as prazosin.

Accordingly in one aspect of the present invention there is provided an isolated, synthetic or recombinant $\rho$-conotoxin peptide having selective $\beta_1$-adrenoceptor antagonist activity.

The $\rho$-conotoxin peptide may be a naturally occurring peptide isolated from a cone snail, or a derivative thereof.

Preferably the $\rho$-conotoxin peptide is $\rho$-TIA or a derivative thereof. $\rho$-TIA may be isolated from the venom duct of the fish hunting cone snail *Conus tulipa*. It is a peptide comprising 19 amino acids and contains two disulphide bonds. The amino acid sequence of $\rho$-TIA is as follows.

FNWRCCLIPACRRNHKKFC
(SEQ ID NO:1)

The C-terminus may be a free acid or amidated.

As used herein the term "selective", unless the context requires otherwise, means that the ability of the peptide to act as an antagonist of an $\beta_1$-adrenoceptor is considerably greater than its ability to act as an antagonist of other $\alpha$-adrenoceptors. Preferably the activity at other $\alpha$-adrenoceptors is negligible.

The term "derivative" as used herein in connection with naturally occurring $\rho$-conotoxin peptides, such as $\rho$-TIA, refers to a peptide which differs from the naturally occurring peptides by one or more amino acid deletions, additions, substitutions, or side-chain modifications. Such derivatives which do not have selective $\beta_1$-adrenoceptor antagonist activity do not fall within the scope of the present invention. One such inactive derivative is the truncated $\rho$-TIA as shown below:

CCLIPACRRNHKKFC
(SEQ ID NO: 2)

Studies of C-terminal truncation of $\rho$-TIA have indicated that the residue at position 4 may be important for binding. Accordingly peptides in which the arginine residue at position 4 is retained or substituted with another amino acid with a positive charge are preferred.

It has also been found that the residues at positions 1, 2 and 3 can be substituted to modify potency and selectivity of $\rho$-TIA. Such modifications include addition or substitution of one or more tyrosine residues which would allow easy labelling of $\rho$-TIA derivatives for assay development.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality or size, for example Ser ⟷ Thr ⟷ Pro ⟷ Hyp ⟷ Gly ⟷ Ala, Val ⟷ Ile ⟷ Leu,   His ⟷ Lys ⟷ Arg, Asn ⟷ Gln ⟷ Asp ⟷ Glu   or Phe ⟷ Trp ⟷ Tyr.

It is to be understood that some non-conventional amino acids may also be suitable replacements for the naturally occurring amino acids. For example ornithine, homoarginine and dimethyllysine are related to His, Arg and Lys.

Substitutions encompassed by the present invention may also be "non-conservative", in which an amino acid residue which is present in a polypeptide is substituted with an amino acid having different properties, such as naturally-occurring amino acid from a different group (eg. substituting a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Preferably, amino acid substitutions are conservative.

Additions encompass the addition of one or more naturally occurring or non-conventional amino acid residues. Deletion encompasses the deletion of one or more amino acid residues.

As stated above the present invention includes peptides in which one or more of the amino acids has undergone side chain modifications. Examples of side chain modifications contemplated by the present invention include modifications of amino groups such as by reductive alkylation by reaction with an aldehyde followed by reduction with $NABH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl groups of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residue may be modified by, for example, hydroxylation in the 4-position.

A list of some amino acids having modified side chains and other unnatural amino acids is shown in Table 1.

TABLE 1

| Non-conventional amino acid | Code |
| --- | --- |
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | |
| cyclopentylalanine | Cpen |

TABLE 1-continued

| Non-conventional amino acid | Code |
| --- | --- |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-a-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) | Nnbhm |

TABLE 1-continued

| Non-conventional amino acid | Code |
|---|---|
| carbamylmethylglycine | |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| Chexa L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methyserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |

TABLE 1-continued

| Non-conventional amino acid | Code |
|---|---|
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethylglycine | Nnbhe |
| O-methyl-L-serine | Omser |
| O-methyl-L-homoserine | Omhser |

These types of modifications may be important to stabilise the peptide if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

The ρ-conotoxins of the present invention are typically amidated at the C-terminal, however compounds with a free carboxyl terminus or other modifications at the C-terminal are considered to be within the scope of the present invention. Preferably the peptides are amidated or have a free carboxyl at the C-terminal.

Preferably the derivatives of naturally occurring ρ-conotoxin peptides will retain the Cys residues and characteristic disulphide bonding pattern. Derivatives may include additional Cys residues provided they are protected during formation of the disulphide bonds.

In modification to form derivatives of naturally occurring ρ-conotoxin peptides it is useful to compare the amino acid sequences of active naturally occurring peptides to determine which, if any, of the residues are conserved between active species. Substitution of these conserved residues, while not prohibited, is less favoured than substitutions of non conserved residues.

Derivatives where Ala replaces one or more residues can be used to identify the pharmacophore. Preferably only one or two amino acids is replaced with Ala at a time. Additional new peptides can be made where charged, polar or hydrophobic residues, respectively, are replaced to assist defining more precisely the type of interactions involved in the binding of this pharmacological class of peptide to its receptor. Non-conservative replacements, where charge is reversed, or polar residues replace hydrophobic residues, can further identify residues involved in binding. All of these peptides have potential to show improved potency, or greater $\alpha_1$-adrenoceptor subtype selectivity. Non-native amino acid changes could also be included to improve potency, selectivity and/or stability.

Exposed residues are most likely to be involved in receptor binding and can be systematically replaced. Particular emphasis is placed on changing residues involved in binding and residues just on the periphery of the pharmacophore, using longer side: chain forms or non-conserved changes to pick up additional binding interactions for improved potency and/or selectivity. Reducing or enlarging loop sizes and the tail of TIA further modifies activity.

It is noted that ρ-TIA is composed of a tail (residues 1–4) and two loops (residues 7–10 and 12–18), however the ρ-conotoxin peptides and derivatives of the present invention are not restricted to those having this particular arrangement of amino acids and disulphide bonds. Other arrangements are also possible, and provided the resultant peptide has selective $α_1$-adrenoceptor antagonist activity, a peptide will fall within the scope of the present invention. Preferably the peptides will have at least two cysteine residues and at lease one disulphide bond, or more preferably four cysteine residues and two disulphide bonds.

The connectivity of the disulfide bonds in these peptides may be A-C/B-D, A-D/B-C or A-B/C-D, the former being preferred for ρ-TIA. A, B, C and D refer to the first, second, third and fourth Cys residues involved in disulphide bond formation, respectively.

These peptides can also be labelled and used to establish binding assays to identify new molecules that act at the same site. For example, labelled ligand of ρ-TIA could have tritium included or may have radio-active iodine or similar attached through a Tyr or other appropriate residue. A Tyr scan through each peptide will establish a suitable location for incorporation of the Tyr. The inhibition of binding of such labelled peptides to tissue homogenates or expressed adrenoceptors by compounds or mixtures would permit identification of new peptides active at this site, including peptides present in serum and nerve and muscle tissue of mammals, including human tissues. The assay will also allow identification of non-peptide molecules that also act at the same site as ρ-TIA, and that may have utility as orally active forms of these peptides. Labelled peptides will additionally permit autoradiographic studies to identify the location of the peptide binding across various tissues.

Portions of these sequences can be used to search ESTR data bases to identify in mammals peptides or proteins that contain related sequence information that could be used to identify endogenous ligands that act in a similar manner in mammals.

The ρ-conotoxins of the present invention may be prepared using standard peptide synthetic methods followed by oxidative disulfide bond formation. For example, the linear peptides may be synthesised by solid phase methodology using BOC chemistry, as described by Schnoltzer et al (1992). Following deprotection and cleavage from the solid support the reduced peptides are purified using preparative chromatography. The purified reduced peptides are oxidised in buffered systems, for example as described in example 2. The oxidised peptides were purified using preparative chromatography.

References describing the synthesis of conotoxins include Sato et al, Lew et al and WO 91/07980.

The ρ-conotoxins may also be prepared using recombinant DNA technology. A nucleotide sequence encoding the desired peptide sequence may be inserted into a suitable vector and protein expressed in an appropriate expression system. In some instances, further chemical modification of the expressed peptide may be appropriate, for example C-terminal amidation. Under some circumstances it may be desirable to undertake oxidative bond formation of the expressed peptide as a chemical step following peptide expression. This may be preceded by a reductive step to provide the unfolded peptide. Those skilled in the art may readily determine appropriate conditions for the reduction and oxidation of the peptide.

The invention further provides an isolated nucleic acid molecule comprising a sequence of nucleotides encoding or complementary to sequence encoding a ρ-conotoxin peptide as described above.

In a further aspect of the present invention there is provided a nucleic acid probe comprising a sequence of nucleotides encoding or complementary to a sequence encoding all or part of a ρ-conotoxin peptide.

In a particularly preferred embodiment the nucleic acid probe comprises a sequence of nucleotides encoding or complementary to a sequence encoding the sequence shown in SEQ ID NO: 1.

As used herein a reference to a "probe" includes reference to a primer used in amplification or a probe for use in direct hybridization.

Still another aspect of the present invention is directed to antibodies to the ρ-conotoxin peptides according to the invention. Such antibodies may be monoclonal or polyclonal and may be selected from naturally occurring antibodies to the peptides or may be specifically raised to the peptides using standard techniques. In the case of the latter, the peptides may first need to be associated with a carrier molecule. The antibodies of the present invent ion are particularly useful as therapeutic or diagnostic agents.

In this regard, specific antibodies can be used to screen for the peptides according to the invention. Techniques for such assays are well known in the art and include, for example, sandwich assays and ELISA. Knowledge of peptide levels may be important for monitoring certain therapeutic protocols.

It may also be possible to prepae antiidiotypic antibodies using techniques known to the art. These antiidiotypic antibodies and their use as therapeutic agents represent a further aspect of the invention.

The nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli Bacillus* sp and *Pseudomonas* sp. Preferred eukaryotic cells include yeast, fungal, mammalian and insect cells.

Accordingly, another aspect of the present invention contemplates a genetic construct comprising a vector portion and a gene capable of encoding a peptide according to the invention.

Preferably, the gene portion of the genetic construct is operably linked to a promoter on the vector such that said promoter is capable of directing expression of the gene portion in an appropriate cell.

The present invention extends to such genetic constructs and to prokaryotic or eukaryotic cells comprising same.

Chimeras of ρ-conotoxins such as ρ-TIA, with other conotoxins or additionally with other peptides or proteins, can be made to engineer the activity into other molecules, in some instances to produce a new molecule with extra functionality. This would preferably be done using the segment or segments of the sequence of these peptides that contain the pharmacophore. Where the pharmacophore is discontinuous, the segments making up the pharmacophore should be positioned in the new construct to allow binding to the receptor. Chimeras with other conotoxins may include additional Cys residues and additional disulphide bonds.

It is common for conotoxin peptides within an activity class to have a similar pattern of disulphide bonding, with peptide loops between the respective cysteine residues. For ρ-TIA disulphide bonds link the first and third, and the second and fourth cysteine residues. This pattern is similar to the binding pattern observed for α-conotoxin peptides. Accordingly chimeric derivatives may be prepared by substituting a loop of a ρ-conotoxin peptide with the loop comprising a sequence from another peptide, including β-conotoxins.

The invention also includes dimers, trimers, etc. of ρ-conotoxin peptides as well as ρ-conotoxin peptides bound to other peptides.

Preferably the ρ-conotoxin peptides according to the invention have 10 to 30 amino acids, more preferably 15 to 25.

The complete gene sequence for the naturally occurring ρ-conotoxin peptides may be obtained using a combined 5' RACE and 3' RACE strategy coupled with cloning and DNA sequencing.

Although ρ-TIA displays some sequence homology to the α-conotoxins, which are nicotinic ACh receptor blockers, ρ-TIA (10 $\mu$M) was not found to target the neuronal or muscle subtype of the nicotinic ACh receptor in assays using isolated preparations of the guinea pig ileum and the mouse phrenic nerve-hemidiaphragm.

Accordingly in a preferred aspect of the present invention the ρ-conotoxin peptide is further characterised by lacking activity at the neuronal or muscle subtype of the nicotinic ACh receptor.

It was also found in binding studies that there is a variation in affinity of ρ-TIA to the $\alpha_{1a}$, $\alpha_{1b}$ and $\alpha_{1d}$-adrenoceptor subtypes. Accordingly in a further aspect of the invention there is provided an isolated, synthetic or recombinant ρ-conotoxin peptide having selective $\alpha_1$-antagonist activity, and having a selectivity for one $\alpha_1$ subtype over the other subtypes.

The ρ-conotoxin peptides according to the present invention are selective $\alpha_1$-adrenoceptor antagonists. Accordingly the invention provides the use of a ρ-conotoxin according to the invention as a selective $\beta_1$-adrenoceptor antagonist, and in the treatment or prophylaxis of diseases or conditions in relation to which antagonist activity at $\alpha_1$-adrenoceptors is associated with effective treatment. Such activity in pharmacological agents is associated with efficacy in the prophylaxis or treatment of diseases or conditions of the urinary or cardiovascular systems, or mood disorders, or in the treatment or control of pain or inflammation.

Accordingly the present invention provides a method for the treatment or prophylaxis of urinary or cardiovascular conditions or diseases or mood disorders, or in the treatment or control of pain or inflammation, including the step of administering to a mammal an effective amount of an isolated, synthetic or recombinant ρ-conotoxin peptide having selective $\alpha_1$-adrenoceptor antagonist activity.

Examples of diseases or conditions of the urinary system include benign prostatic hyperplasia and related disorders. Examples of cardiovascular diseases or conditions include arrhythmia of various regions, hypertension and coronary heart failure. Examples of mood disorders include cravings such as smoking. Examples of pain include chronic pain, neuropathic pain and inflammatory pain.

Preferably the mammal is in need of such treatment although the peptide may be administered in a prophylactic sense.

The invention also provides a composition comprising an isolated, synthetic or recombinant ρ-conotoxin peptide having selective $\beta_1$-adrenoceptor antagonist activity, and a pharmaceutically acceptable carrier or diluent.

Preferably the composition is in the form of a pharmaceutical composition.

There is also provided the use of an isolated, synthetic or recombinant ρ-conotoxin peptide having selective $\beta_1$-adrenoceptor antagonist activity in the manufacture of a medicament for the treatment or prophylaxis of urinary or cardiovascular conditions or diseases, or mood disorders or for the treatment or control of pain or inflammation.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives care should be taken to ensure that the activity of the peptide is not destroyed in the process and that the peptide is able to reach its site of action without being destroyed. In some circumstances it may be necessary to protect the peptide by means known in the art, such as, for example, micro encapsulation. Similarly the route of administration chosen should be such that the peptide reaches its site of action.

The pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

Those skilled in the art may readily determine appropriate formulations for the peptides or modified peptides of the present invention using conventional approaches. Identification of preferred pH ranges and suitable excipients, for example antioxidants, is routine in the art (see for example Cleland et al, 1993). Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminum monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various of the other ingredients such as these enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying a of a previously sterile-filtered solution of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to any other forms suitable for administration, for example topical application such as creams, lotions and gels, or compositions suitable for inhalation or intranasal delivery, for example solutions or dry powders.

Parenteral dosage forms are preferred, including those suitable for intravenous, intrathecal, intracerebral or epidural delivery.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.25 $\mu$g to about 2000 mg. Expressed in proportions, the active compound is generally present in from about 0.25 $\mu$g to about 200 mg/ml of carrier. In the case of compositions containing supplementary active ingredients, the dosages are determined by reference to the usual dose and manner of administration of the said ingredients.

The invention will now be described with reference to the accompanying drawings and examples, however it is to be understood that the particularity of the following description is not to supersede the generality of the preceding description of the invention.

Referring to the figures:

FIG. 1 is a graphical representation showing the effect of $\rho$-TIA on the time course of the isometric contraction of a representative preparation of bisected rat prostatic vas deferens subjected to field stimulation with a single supramaximal pulse (55 V, 1 ms). $\rho$-TIA (100 nM–3 $\mu$M) was added to the organ bath cumulatively using a half log unit dose progression.

Figure 2:
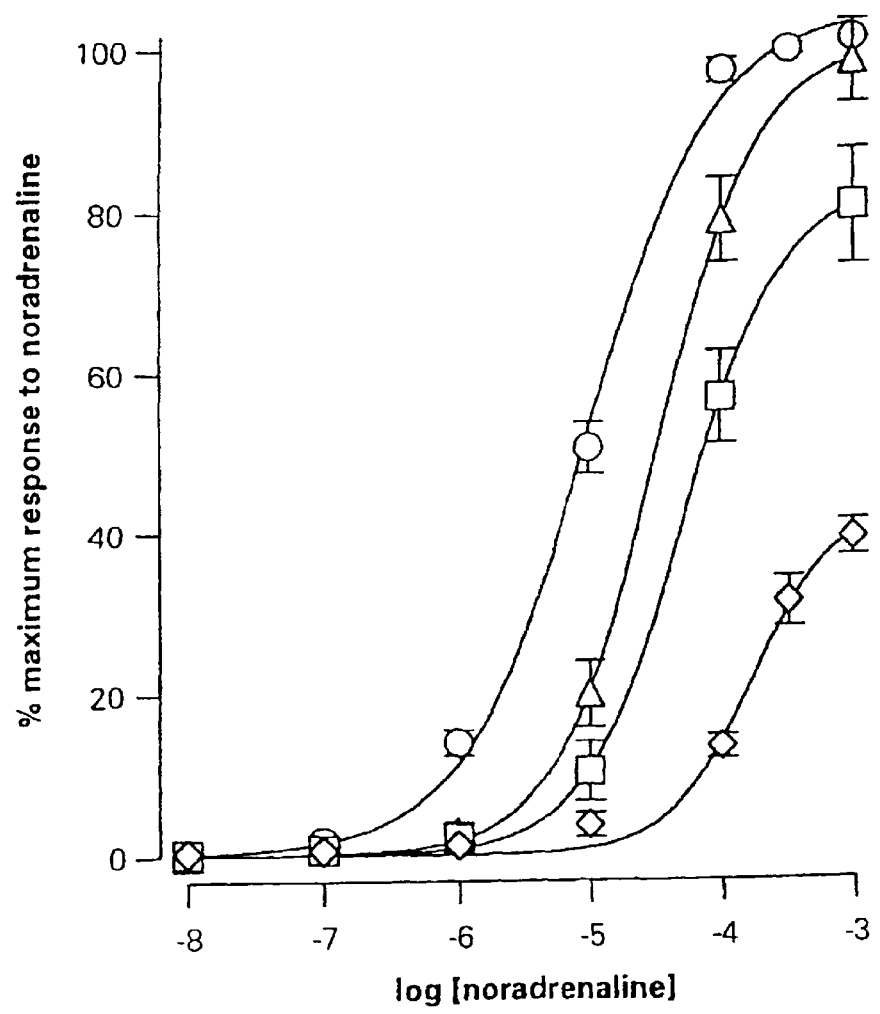

FIG. 2 is a graphical representation showing the log concentration-response curves for noradrenaline in the bisected rat epididymal vas deferens in the absence (O) and presence of 1 $\mu$M ($\Delta$), 3 $\mu$M ($\square$) or 10 $\mu$M ($\Diamond$) $\rho$-TIA. Data points are the means±SEM of responses from 5 separate experiments. Some error bars are obscured by the symbols.

Figure 3:
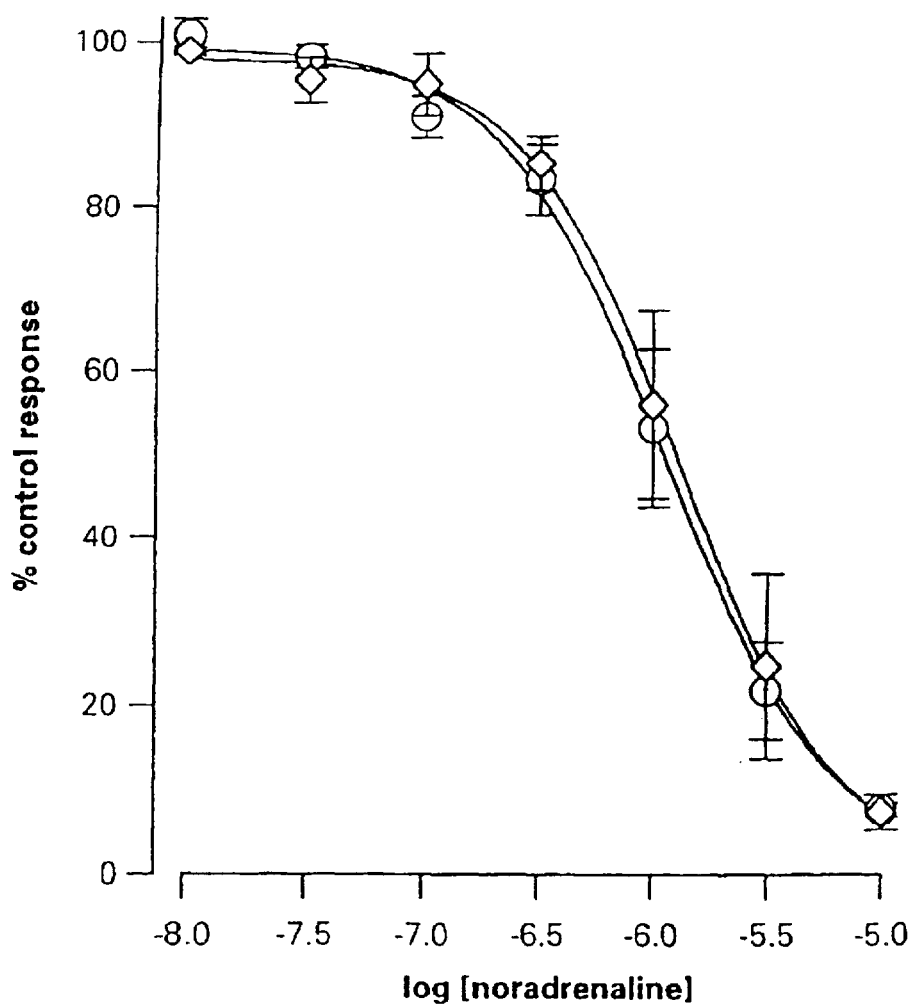

FIG. 3 is a graphical representation of the effect of $\rho$-TIA on the $\alpha_2$-adrenoceptor mediated inhibition of the twitch response of the bisected rat prostatic vas deferens to field stimulation with a single supramaximal pulse (55 V, 1 ms). Log concentration-response curves for noradrenaline in the absence (O) and presence ($\Diamond$) of 10 $\mu$M $\rho$-TIA. Each point is the mean of 5 experiments and the vertical bars indicate the SEM.

Figure 4:
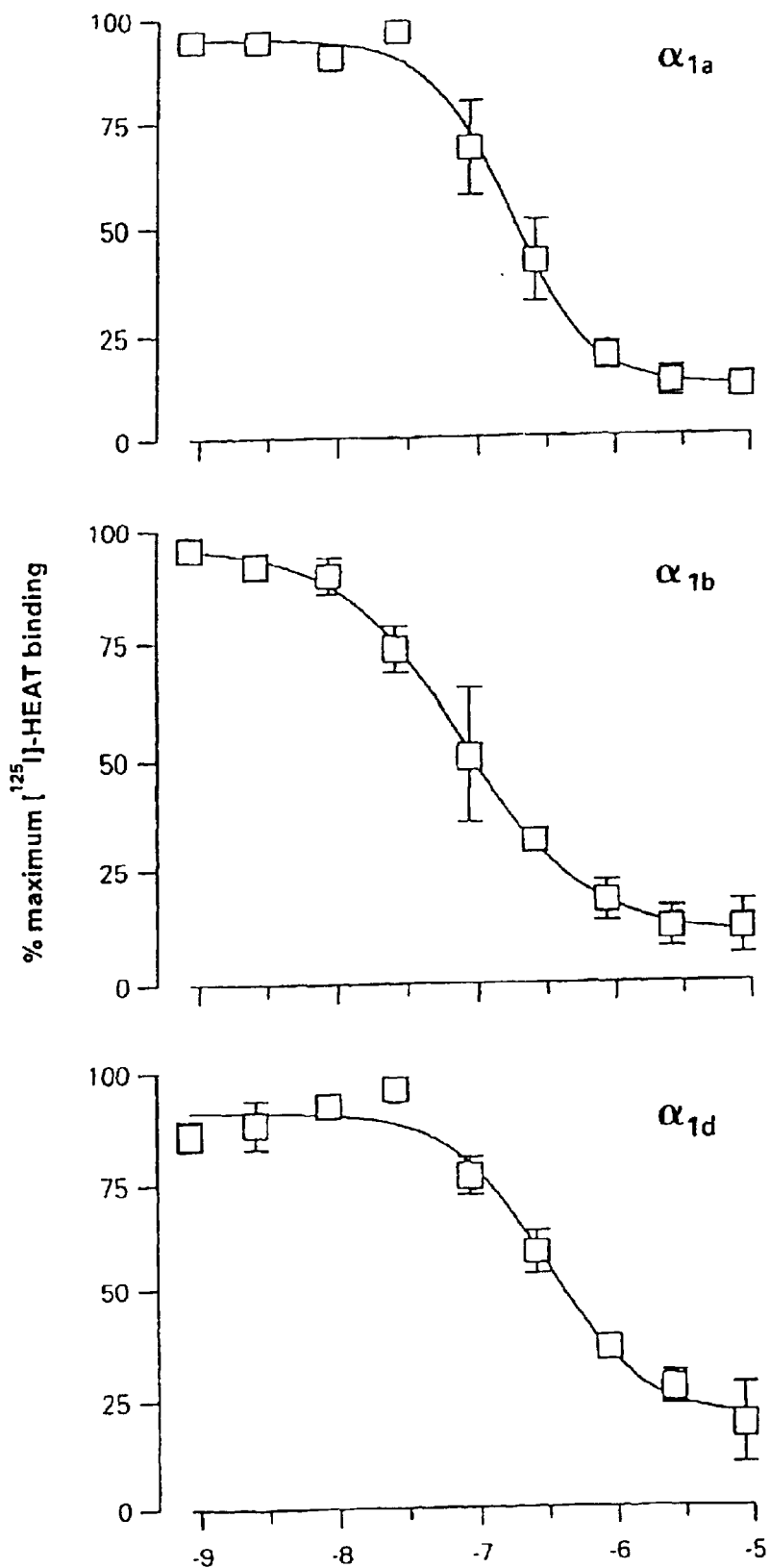

FIG. 4 is a graphical representation of the effect of $\rho$-TIA on the binding by the radiolabelled $\beta_1$-adrenoceptor antagonist [$^{125}$I]-HEAT to membrane preparations from COS-1 cells transiently transfected with cDNA clones for the three $\beta_1$-adrenoceptor subtypes, $\alpha_{1a}$, $\alpha_{1b}$ and $\alpha_{1d}$. Each point represents the mean from three experiments ±SEM. Some error bars are obscured by the symbols.

Figure 5:
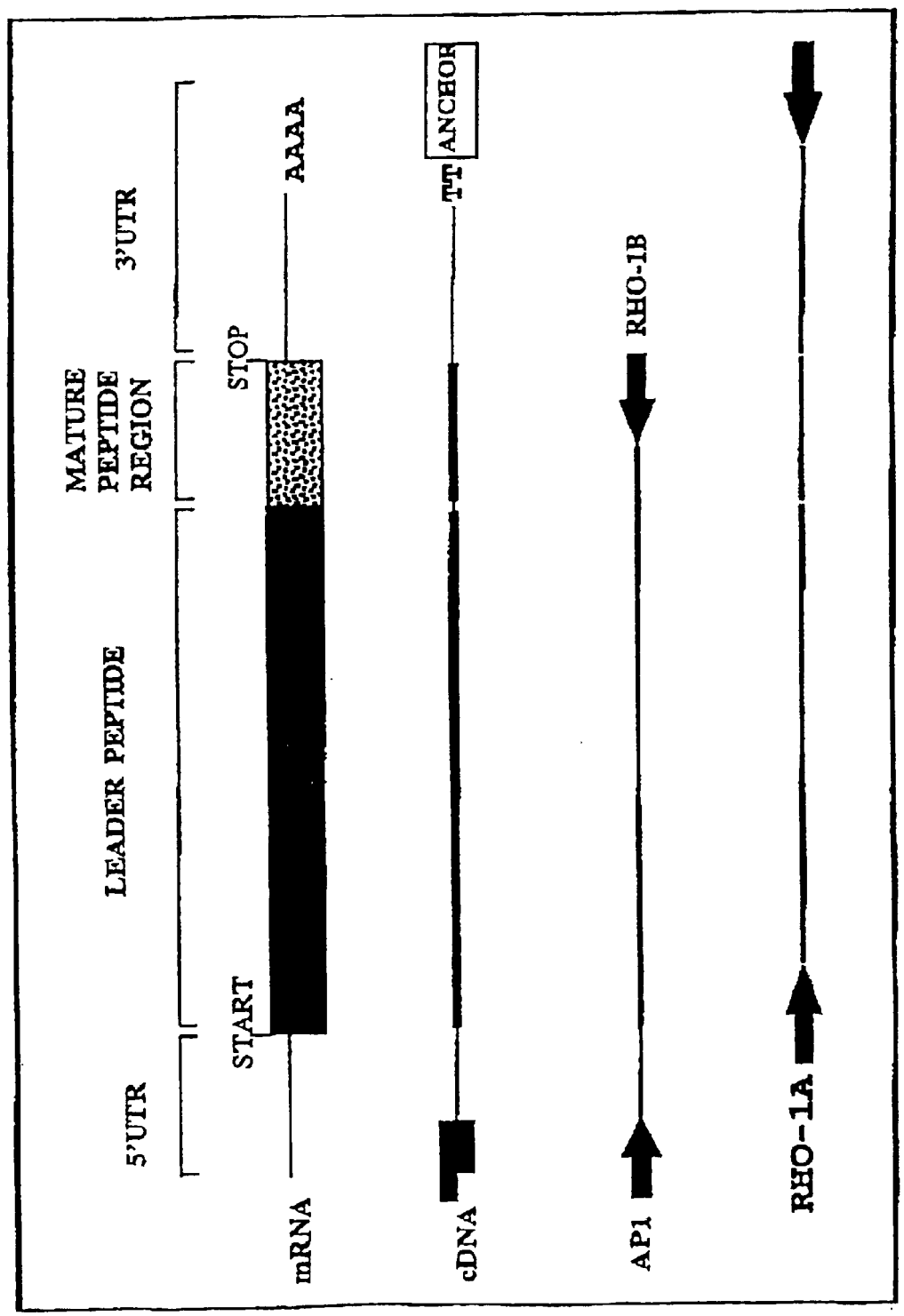

FIG. 5 is a diagrammatic representation showing the derivation of coneshell venom peptide sequences. 5' RACE PCR using the primers AP1+RHO-1B produce the 5' UTR and leader peptide sequence which is then used to generate PCR primers specific for $\rho$-conotoxins. The 3' UTR using the primers RHO-1A+ANCHOR completed the derivation of the remaining mature peptide sequence and the 3' UTR sequence.

EXAMPLES

Statistics and Data Analysis

Data for the following examples were expressed as mean±s.e. of the mean from results obtained from n=3–6 experiments. Student's two-tailed t test or ANOVA were used for statistical evaluation and values of p<0.05 were considered significant. Sigmoidal curve-fitting of concentration-response curves for the calculation of $EC_{50}$ values was done by non-linear regression using the software package Igor Pro (WaveMetrics). Radioligand binding data were analysed using the iterative non-linear curve-fitting program !Prism (GraphPad). $IC_{50}$ values were converted to Ki values using the Cheng-Prusoff equation and a $K_D$ for [$^{125}$I]-HEAT of 66 pM.

Drugs

The following drugs were obtained from Sigma: indomethacin, nicotine hydrogen tartrate, (−)-noradrenaline bitartrate, prazosin hydrochloride, suramin, tetrodotoxin, and yohimbine hydrochloride. [$^{125}$I]-HEAT (specific activity 2200 Ci/mmol) was obtained from New England Nuclear.

Example 1

Rat Vas Deferens

Male Wistar rats (250–350 g) were killed by a blow to the head and exsanguinated. The vasa deferentia were removed and trimmed of connective tissue. Each vas deferens was cut into bisected epididymal and prostatic segments. The tissue portions were mounted under a tension of 0.5 g in 5 mL organ baths containing a physiological salt solution at 37° C. and bubbled with 5% v/v $CO_2$ in $O_2$. The composition of the bathing solution was (mM): NaCl, 119; KCl, 4.7; $MgSO_4$, 1.17; $KH_2PO_4$, 1.18; $NaHCO_3$, 25.0; glucose, 5.5; $CaCl_2$, 2.5; EDTA, 0.026. The tissue preparations were allowed to equilibrate for at least 45 min prior to experimentation. Isometric contractions were registered using a force transducer (Narco Bio-System F-60), and were recorded digitally on a Power Macintosh computer with Chart version 3.5.4/s software and a MacLab/8s data acquisition system (ADInstruments) at a sampling frequency of either 10 or 200 Hz.

The bisected prostatic segments were placed between two platinum stimulating electrodes. To examine the effect of ρ-TIA on the electrically evoked contraction of the smooth muscle mediated by sympathetic neurotransmission, increasing concentrations of the peptide: were added cumulatively to the organ bath as the tissue was being subjected to electrical field stimulation. Single electrical pulses of amplitude 55 V and duration 1 ms were generated by a Grass S44 stimulator at 3 min intervals. The resulting contractions could be abolished by tetrodotoxin (0.1 μM), indicating that they were neurogenic in origin. Furthermore, the initial phase of the contraction was sensitive to suramin (0.3 mM) and the second phase could be inhibited by prazosin (0.5 μM).

Effect of ρ-TIA on Sympathetic Neurotransmission in the Rat Vas Deferens

The response of the bisected rat prostatic vas deferens to field stimulation was biphasic. The first phase of the contraction was the larger of the two, and peaked approximately 200 ms after stimulation. The second phase reached a maximum approximately 500–600 ms after the stimulus. ρ-TIA acted to reduce the second phase of the contraction in a concentration dependent manner (FIG. 1). The monophasic peak generated by subtracting the trace obtained in the presence of the highest concentration of ρ-TIA used (10 μM) from the others, illustrates that the effect of the conotoxin was specific for only the second component of the contraction. The concentration of conotoxin that inhibits the second phase of the contraction by 50%, the $IC_{50}$ value, was found to be approximately 300 nM (FIG. 1)

The pattern of inhibition caused by ρ-TIA resembles that observed using prazosin or other $β_1$-adrenoceptor antagonists (McGrath, 1978, J Physiol Lond, 283, 23–39). It has been noted however, that when high concentrations of prazosin (0.5 μM) are used, the specificity of action is lost, with the first component of the contraction also sensitive to inhibition. The first component is mediated by the action of the sympathetic co-transmitter ATP at $P_{2x}$-purinoceptors, and can be abolished by $P_{2x}$-purinoceptor antagonists such as suramin. It is therefore considered likely that the non-specific inhibition of the first phase of the contraction is due to blockade of neuronal $Na^+$ channels, a local anaesthetic effect which has been previously reported for prazosin and some other $β_1$-adrenoceptor antagonists (Bralet et al., 1985, Br J Pharmacol, 84, 47–55; Northover, 1983, Br J Pharmacol, 80, 85–93; Perez et al., 1994, Mol Pharmacol, 46, 823–31). ρ-TIA acted as a functional non-competitive antagonist, suggesting that it acted allosterically at a new site to modulate noradrenaline binding to the $β_1$-adrenoceptor.

Example 2

Effects of Post-Junctional Responses Methods

These experiments were similar to those described in Example 1 except that the bisected epididymal segments were not electrically stimulated. These tissue preparations were used to examine the effect of ρ-TIA on the post-junctional contractile response to noradrenaline. Cumulative concentration-response curves were established in the absence and presence of ρ-TIA. The conotoxin, at a concentration of either 1 μM, 3 μM or 10 μM, was added to the organ bath and equilibrated with the tissue for 20 min prior to the application of doses of noradrenaline. A single concentration-response curve was generated per preparation, with contralateral tissue segments which were not exposed to ρ-TIA serving as controls.

Effect of ρ-TIA on the Response to Noradrenaline in the Rat Vas Deferens

To confirm that the effect of ρ-TIA on the response to field stimulation was due to the action of the peptide downstream of neurotransmitter release, its effect on the response to exogenously applied noradrenaline was examined.

Log concentration-response curves to noradrenaline on bisected segments of the rat epididymal vas deferens were generated in the absence and presence of ρ-TIA (FIG. 2). The effect of ρ-TIA at a concentration of 1 μM was a three-fold reduction in the sensitivity of the tissue to noradrenaline, observed as a shift of the concentration-response curve to the right. At higher concentrations (3 μM and 10 μM) ρ-TIA acted to reduce the sensitivity of the tissue further, increasing the $EC_{50}$ of noradrenaline by a factor of 5.2 and 16.7. The two highest concentrations of ρ-TIA also acted to depress the level of the maximum response to 82 and 42% of the control response, respectively.

The reduction of the maximal response of the vas deferens to noradrenaline caused by ρ-TIA is consistent with the conotoxin acting as a non-competitive $β_1$-adrenoceptor antagonist. Initially, the noradrenaline concentration response curve is shifted to the right without any change in the maximum tension developed. As the concentration of ρ-TIA is increased, further shifting of the curve to the right accompanies the progressive decline in the maximum response. These results indicate the existence of a pool of "spare" $α_1$-adrenoceptors in this tissue, and supports the findings of Diaz-Toledo & Marti 1988 Eur J Pharmacol, 156, 315–24, and Minneman & Abel 1984, Mol Pharmacol, 25, 56–63, who demonstrated a functional reserve of α-adrenoceptors in the rat vas deferens. Although it acts in a non-competitive manner, ρ-TIA is not an irreversible antagonist, as there is slow recovery from the inhibition of the electrically evoked response of the vas deferens caused by the conotoxin upon washing of the preparation with drug-free solution.

Example 3

Experiments to Examine the Effect of ρ-TIA on $\alpha_2$-Adrenoceptors

Similar experimental protocol to Example 1 was followed, except that electrical field stimulation was made with single pulses of the same duration and amplitude, but at 20 s intervals. In the presence of prazosin (0.5 µM), a cumulative concentration-response curve for noradrenaline causing inhibition of the twitch response was established. Upon washout and recovery, the prazosin was replaced, and ρ-TIA (10 µM) was applied to the organ bath. After an equilibration period of 20 min, a second concentration-response curve to noradrenaline was generated.

Effect of ρ-TIA on Presynaptic Inhibition of Neurotransmitter Release in the Rat Vas Deferens The release of the sympathetic co-transmitters ATP and noradrenaline from neuronal stores is subject to modulation by the activation of presynaptic $\alpha_2$-adrenoceptors (Amobi & Smith, 1988, J Auton Pharmacol, 8, 141–52; McCulloch et al., 1985 Br J Pharmacol, 86, 455–64). To determine whether ρTIA acts to block $\beta_2$-adrenoceptors, its effect on the inhibition by noradrenaline of the purinergic contraction of segments of the rat vas deferens was examined. $\alpha_2$-adrenoceptor antagonist drugs such as yohimbine, antagonize the inhibitory effect of noradrenaline in this assay (Warming et al., 1982 Arch Int Pharmacodyn Ter, 259, 14–30).

The response of the vas deferens to electrical stimulation in the presence of prazosin was inhibited by noradrenaline with a –log $IC_{50}$ value of 5.96±0.052 (FIG. 3). This value was not significantly different from the value of the –log $IC_{50}$ determined in the presence of 10 µM ρ-TIA. (5.90±0.031, p>0.3, n=5).

It was found that ρ-TIA did not antagonize the action of noradrenaline at $\alpha_2$-adrenoceptors. ρ-TIA is capable therefore of discriminating between $\alpha_1$ and $\alpha_2$-adrenoceptors.

Example 4

Guinea-Pig Ileum

Male guinea-pigs (285–425 g) were starved overnight then killed by a blow to the head and exsanguinated. Segments approximately 1.5 cm long were taken from the ileum, and the luminal contents removed by gentle washing with bathing solution. The preparations were mounted under a resting tension of 1.0 g in 5 mL organ baths. The bathing solution contained (mM): NaCl, 136.9; KCl, 2.68; $CaCl_2$, 1.84; $MgCl_2$, 1.03; glucose, 5.55; $NaHCO_3$, 11.9; and $KH_2PO_4$, 0.45; was warmed to 37° C. and bubbled with 5% v/v $CO_2$ in $O_2$. Indomethacin (10 µM) was included in the bathing solution to maintain a stable baseline. After an equilibration period of at least 40 min, doses of nicotine (4 µM) were added at 15 min intervals. When the contractile response to nicotine was found to be reproducible, the tissue was exposed to ρ-TIA for 25 min. After this time, another dose of nicotine was applied. The responses to nicotine were measured isometrically and digitized at a sampling rate of 10 Hz.

Effect of ρ-TIA on Responses to Nicotine in the Guinea-Pig Ileum

The responses of ileal segments to nicotine were not significantly affected by ρ-TIA (10 µM). In the absence of ρ-TIA, the mean response was 3.29±0.67 g, and in the presence of ρ-TIA was 4.13±0.70 g p>0.25; paired t-test; n=4).

The present finding that the response of segments of guinea-pig ileum to nicotine and the response of the mouse phrenic nerve-hemidiaphragm to electrical stimulation are not affected by ρ-TIA indicate that unlike the α-conotoxins, this novel conotoxin does not target either the neuronal or muscle subtype of the nicotinic ACh receptor.

Example 5

Mouse Phrenic Nerve-Hemidiaphragm

Left and right hemidiaphragms, with the phrenic nerves attached, were removed from male Quackenbush mice (20–30 g) killed by cervical dislocation. The base of each hemidiaphragm was positioned between two parallel platinum stimulating electrodes and the phrenic nerve was placed through two small platinum loops for field stimulation. The preparations were mounted in 5 mL organ baths under a tension of 1.0 g, and bathed in a solution of the following composition (mM): NaCl, 135.0; KCl, 5.0; $CaCl_2$, 2.0; $MgCl_2$, 1.0; glucose, 11.0; $NaHCO_3$, 15.0; and $KH_2PO_4$, 1.0. The bathing solution was heated to 37° C. and continuously bubbled with 5% v/v $CO_2$ in $O_2$. Following an equilibration period of at least 30 min, alternating direct and indirect stimulation was made at 10 s intervals. Direct stimulation was made using a 30 V pulse of 2 ms duration delivered to the electrodes placed against either side of the muscle, and indirect stimulation was made with a 3 V pulse of 0.2 ms duration delivered to the electrodes surrounding the phrenic C nerve. The effect of a single dose of ρ-TIA at a concentration of 10 µM on these directly and indirectly evoked responses was examined. The contractions were recorded in the same manner as described for the vas deferens preparations.

Effect of ρ-TIA on Responses to Electrical Stimulation of the Mouse Phrenic Nerve-Hemidiaphragm ρ-TIA (10 µM) did not affect contractions of the mouse hemidiaphragm elicited by field stimulation of the phrenic nerve or by direct muscle stimulation (n=4; data not shown) indicating that ρ-TIA does not target the muscle nicotinic ACh receptor.

Example 6

Radioligand Binding Studies

The α-adrenoceptor constructs used were the rat $\alpha_{1A}$-AR cDNA, the hamster $\alpha_{1B}$-AR cDNA and the rat $\alpha_{1D}$-cDNA cloned into the modified eukaryotic expression vector, pMT2', as described previously (Hwa et al., 1995, J Biol Chem, 270, 23189–95; Perez et al., 1991, Mol Pharmacol, 40, 876–83; Perez et al., 1994, Mol Pharmacol, 46, 823–31). COS-1 cells (American Type Culture Collection) were cultured and transiently transfected with the constructs using the DEAE-dextran method (Cullen, 1987, Methods Enzymol, 152, 684–704). Transfection efficiency for this method ranges from 30 to 40%. Cells were harvested 72 h after transfection. Membranes were prepared from transfected COS-1 cells, as described previously (Perez et al., 1991, Mol Pharmacol, 40, 876–83). The membranes were resuspended in HEM buffer (20 mM HEPES, pH 7.5, 1.5 mM EGTA, 12.5 mM $MgCl_2$ containing 10% (v/v) glycerol and stored at –70° C. The ligand binding characteristics of the expressed receptors were determined in a series of radioligand binding studies using [$^{125}$I]-HEAT, a specific $\beta_1$-adrenoceptor antagonist. The procedure involved duplicate tubes containing COS-1 cell membranes, 70 pM [$^{125}$I]-HEAT, HEM buffer, and π-TIA (at 9 different concentrations) in a total reaction volume of 250 µL. Non-specific binding was determined in the presence of phentolamine (100 µM). After 1 h of incubation at room temperature, the reactions were stopped by the addition of ice-cold HEM buffer and were filtered onto Whatman GF/C glass filters with a Brandel cell harvestor. The filters were washed 5 times with ice-cold HEM buffer. The amount of bound radioactivity was analysed using a Packard Auto-gamma 500 Counter.

Effect of ρTIA in Radioligand Binding Studies

The $\beta_1$-adrenoceptors are a heterogenous family, and three distinct subtypes, $\alpha_{1A}$, $\alpha_{1B}$ and $\alpha_{1D}$, have been cloned. The action of ρ-TIA in the radioligand binding studies was to inhibit the binding of [$^{125}$I]-HEAT to the three expressed $\beta_1$-adrenoceptor subtypes, confirming that the $\beta_1$-adrenoceptor is the target of the conotoxin (FIG. 4). The $-\log K_i$ values were determined to be 7.29±0.141 for the $\alpha_{1A}$ subtype; 7.70±0.179 for the $\alpha_{1B}$ subtype; and 7.09±0.057 for the $\alpha_{1D}$ subtype. The difference in the potency of ρ-TIA at $\alpha_{1B}$ and $\alpha_{1D}$-adrenoceptors was found to be significant (p<0.05), indicating that ρ-TIA and analogs have the potential to distinguish among $\beta_1$-adrenoceptor subtypes.

ρ-TIA was most potent at the $\alpha_{1B}$-adrenoceptor subtype. The $K_i$ value of 20 nM indicated that ρ-TIA is approximately 2 orders of magnitude less potent than the classical $\beta_1$-adrenoceptor antagonist prazosin at this subtype based on data reported in the literature. The discovery of subtype specific antagonists is of interest for their potential usefulness both as research tools to investigate the structure and functioning of $\alpha_1$-adrenoceptors, and as potential therapeutic agents for the treatment of such conditions as benign prostatic hyperplasia (Chapple, 1995, Br J Urol, 1, 47–55). Radioligand binding studies further indicated that ρ-TIA acted non-competitively to inhibit [$^{125}$I]-HEAT binding, indicative of an allosteric modulator acting at a site separate from the noradrenaline binding site on the $\alpha_1$-adrenoceptor.

In conclusion, there are many structural classes of compounds that have the capacity to act as $\beta_1$-adrenoceptor antagonists. Among these classes are the alkaloids, a group which comprises a number of natural products. These include dicentrine (Teng et al., 1991, Br J Pharmacol, 104, 651–6), and dehydroevodiamine (Chiou et al., 1996, J Cardiovasc Pharmacol, 27, 845–53) isolated from plant sources, and hymenin, an alkaloid isolated from a sea sponge (Kobayashi et al., 1986, Experientia, 42, 1064–5). Another $\beta_1$-adrenoceptor antagonist isolated from a species of sea sponge is aaptamine. Unlike hymenin, aaptamine is not an alkaloid, but is rather a heteroaromatic compound (Ohizumi et al., 1984, J Pharm Pharmacol, 36, 785–6). These alkaloids do not act with a high degree of specificity, and antithrombotic and local anaesthetic actions have been observed in addition to $\alpha_1$-adrenoceptor blockade. ρ-TIA is structurally distinct from all of these existing small organic molecules, both natural and synthetic, in that it is the only example to date of a peptide $\beta_1$-adrenoceptor antagonist. Additionally, ρ-TIA is the first conotoxin found to target the $\beta_1$-adrenoceptor, and so represents the first member of a novel class of peptides which we designate the ρ-conotoxin family.

Example 7
Derivation of Gene Sequence for the ρ-Conotoxin Peptides

The complete gene sequence for the ρ-conotoxin was isolated using a combined 5' RACE (Random Amplification of cDNA Ends) and 3' RACE strategy coupled with cloning and DNA sequencing.

5' RACE

The oligonucleotide primer RHO-1B was designed from the mature ρ-TIA peptide sequence. The relationship of the oligonucleotide to the peptide is as follows, together with the oligonucleotide sequence:

| | | |
|---|---|---|
| ρ-TIA (SEQ ID NO: 1) | - | FNWRCCLIPACRRNHKKFC |
| HO-1B (SEQ ID NO: 3) | 5'- | RCARAAYTTYTTRTGRTT-3' |
| AP1 (SEQ ID NO: 4) | 5'- | CCATCCTAATACGACTCACTATAGGGC-3' |

(where N=A/C/G/T, R=A/G, Y=C/T,)

Polymerase Chain Reaction (PCR) was carried out using the oligonucleotide RHO-1B in combination with the AP1 oligonucleotide on cDNA templates derived from the mRNA isolated from coneshell venom ducts. The PCR products, which represent the 5' region of the ρ-TIA gene were isolated, purified, cloned into bacterial vectors and sequenced. Gene sequence for ρ-TIA was obtained from C. tupila (FIG. 5).

3' RACE

The DNA sequence for the 5' regions of the ρ-TIA gene was used to design oligonucleotides that were capable of detecting the ρ-TIA sequence, and sequence from other closely related peptides. The positioning of the oligonucleotides relative to the gene sequence is shown in FIG. 5. The oligonucleotide RHO-1A is used in PCR in conjunction with the ANCHOR oligonucleotide to produce DNA fragments corresponding to the leader peptide, mature peptide and 3' untranslated (3' UTR) regions of the gene. PCR of venom duct cDNA templates from C. tulipa produce DNA fragments corresponding to ρ-TIA.

The DNA sequences for ANCHOR is:

| | |
|---|---|
| ANCHOR (SEQ ID NO: 5) | 5'-AACTGGAAGAATTCGCGGCCGCAGGAAT-3' |

Complete Sequence for ρ-TIA

Gene sequence for ρ-TIA produced using 5' RACE and 3' RACE represent overlapping fragments of the gene. These fragments are combined, to produce a consensus sequence for each gene. The consensus sequences are the full cDNA for the genes, and include 5' UTR, the leader peptide, the mature peptide and the 3' UTR.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. An isolated, synthetic or recombinant ρ-conotoxin peptide having selective $\beta_1$-adrenoceptor antagonist activity whereby the ability of said peptide to inhibit the agonist action of nor-adrenaline at an $\alpha_1$-adrenoceptor is greater than its ability to inhibit the agonist action of nor-adrenaline at other α-adrenoceptors.

2. A ρ-conotoxin peptide according to claim 1 having the sequence of SEQ ID NO: 1 (FNWRCCLIPACRRNHKKFC), or a sequence that differs from SEQ ID NO: 1 by having at least one amino acid deletion, addition, substitution or side chain modification.

3. A ρ-conotoxin peptide according to claim 2 which is ρ-TIA.

4. A ρ-conotoxin peptide according to claim 1 having no or negligible activity at the neuronal or muscle subtype of nicotinic acetylcholine receptor.

5. A ρ-conotoxin peptide according to claim 1 having selective antagonist activity for one $\alpha_1$-adrenoceptor subtype over other subtypes of $\beta_1$-adrenoceptors.

6. A ρ-conotoxin peptide according to claim 1 having four cysteine residues and two disulphide bonds.

7. A ρ-conotoxin peptide according to claim 6 wherein the disulphide bond connectivity is A-C/B-D, where A, B, C and D refer to the first, second, third and fourth cysteine residue, respectively.

8. A ρ-conotoxin peptide according to claim 1 which is a chimeric peptide comprising a segment of a naturally occurring ρ-conotoxin peptide and a segment of another biologically active peptide or protein, wherein the said chimeric peptide possesses an activity of said another biologically active peptide or protein.

9. A composition comprising an isolated, synthetic or recombinant ρ-conotoxin peptide having selective $\alpha_1$-adrenoceptor antagonist activity, and a pharmaceutically acceptable carrier or diluent, whereby the ability of said peptide to inhibit the agonist action of nor-adrenaline at an $\alpha_1$-adrenoceptor is greater than its ability to inhibit the agonist action of nor-adrenaline at other $\alpha$-adrenoceptors.

10. A composition according to claim 9 which is a pharmaceutical composition.

11. A composition according to claim 9 whereby said peptide has selective antagonist activity for one $\alpha_1$-adrenoceptor subtype over other subtypes of $\beta_1$-adrenoceptors.

* * * * *

SEQUENCE LISTING

<160> NUMBER OF SEQ ID NOS: 5

<210> SEQ ID NO 1
<211> LENGTH: 19
<212> TYPE: PRT
<213> ORGANISM: Conus tulipa

<400> SEQUENCE: 1

Phe Asn Trp Arg Cys Cys Leu Ile Pro Ala Cys Arg Arg Asn His Lys
 1               5                  10                  15

Lys Phe Cys

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Derivative
      of ρ-conotoxin of SEQ ID NO:1.

<400> SEQUENCE: 2

Cys Cys Leu Ile Pro Ala Cys Arg Arg Asn His Lys Lys Phe Cys
 1               5                  10                  15

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer designed based on the mature ρ-TIA peptide
      sequence (SEQ ID NO:1).

<400> SEQUENCE: 3
rcaraaytty ttrtgrtt                                                 18

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer AP1, used in the 5' RACE for cloning the
      ρ-conotoxin gene.

<400> SEQUENCE: 4
ccatcctaat acgactcact atagggc                                       27

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide primer ANCHOR, used in the 3' RACE for cloning the
      ρ-conotoxin gene.

<400> SEQUENCE: 5
aactggaaga attcgcggcc gcaggaat                                      28